(12) United States Patent  
Mansor et al.

(10) Patent No.: US 9,289,525 B1  
(45) Date of Patent: Mar. 22, 2016

(54) TIME RELEASE BIOCIDE DISPENSING DEVICE

(71) Applicants: Simo Mansor, Lauderhill, FL (US); Bassem Alhalabi, Boca Raton, FL (US)

(72) Inventors: Simo Mansor, Lauderhill, FL (US); Bassem Alhalabi, Boca Raton, FL (US)

(73) Assignee: Simo Mansor, Lauderhill, FL (US)

( * ) Notice: Subject to any disclaimer, the term of this patent is extended or adjusted under 35 U.S.C. 154(b) by 0 days.

(21) Appl. No.: 14/474,885

(22) Filed: Sep. 2, 2014

(51) Int. Cl.
| | |
|---|---|
| *B01D 11/02* | (2006.01) |
| *A61L 2/00* | (2006.01) |
| *C02F 1/68* | (2006.01) |
| *B01D 21/24* | (2006.01) |
| *A61L 2/18* | (2006.01) |

(52) U.S. Cl.  
CPC .......................................... *A61L 2/18* (2013.01)

(58) Field of Classification Search  
CPC .................................. A61L 2/00; A01N 63/00  
USPC ........ 422/28, 32–33, 261, 292; 210/749, 764, 210/97, 153; 134/6  
See application file for complete search history.

(56) References Cited

U.S. PATENT DOCUMENTS

2006/0137127 A1* 6/2006 Field ...................... A47L 13/26  
15/320

* cited by examiner

*Primary Examiner* — Monzer R Chorbaji

(57) ABSTRACT

A time release biocide dispensing device for controllably dispensing biocide into a condensation line of an air conditioner at predetermined concentrations and volumes over a duration. The device utilizes principles of pressure equilibrium and material resistance to dispense a regulated and steady flow of the biocide into the line. The device utilizes a controller, a pump, a container, a fluid tube, and a coupling member. The device is configured to easily attach to the line and facilitate setting of the controller, such that minimal tools and expertise are needed for operation. A container attaches to the line and holds a biocide and a volume having a vacuum. A pump forces a fluid into the vacuum to disturb the equilibrium, and thus partially force the biocide into the line. A resistance member restricts the flow to drops to further regulate the flow of the biocide into the line.

20 Claims, 3 Drawing Sheets

TIME RELEASE BIOCIDE DISPENSING DEVICE

FIELD OF THE INVENTION

Figure 1:
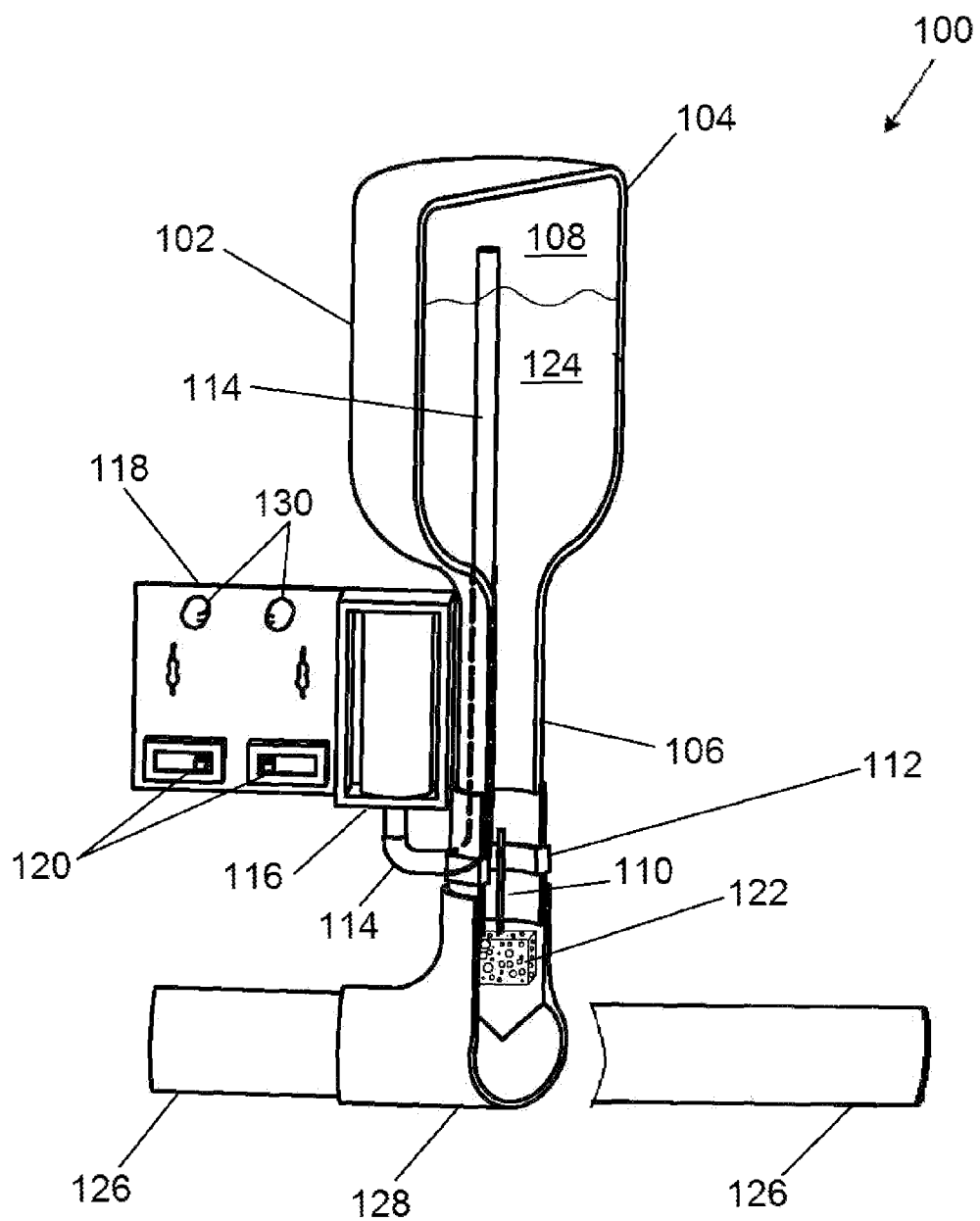

The present invention relates generally to a time release biocide dispensing device. More so, a time release biocide dispensing device regulates the release of a biocide into a condensation line by controllably pumping a fluid into a vacuum that is formed in a container above the biocide to displace the biocide through a resistance barrier, and into the condensation line.

BACKGROUND OF THE INVENTION

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon.

The following is an example of a specific aspect in the prior art that, while expected to be helpful to further educate the reader as to additional aspects of the prior art, is not to be construed as limiting the present invention, or any embodiments thereof, to anything stated or implied therein or inferred thereupon.

By way of educational background, another aspect of the prior art generally useful to be aware of is that air conditioning is the process of altering the properties of air (primarily temperature and humidity) to more comfortable conditions, typically with the aim of distributing the conditioned air to an occupied space to improve thermal comfort and indoor air quality. This involves a refrigeration cycle that carries fluids through a coils, condensation lines, and various other refrigerant components.

In the refrigeration cycle, heat is transported from a colder location to a hotter area. As heat would naturally flow in the opposite direction, work is required to achieve this. A refrigerator is an example of such a system, as it transports the heat out of the interior and into its environment, such as a room. The refrigerant is used as the medium which absorbs and removes heat from the space to be cooled and subsequently rejects that heat elsewhere.

Typically, the cycle continues as the circulating refrigerant vapor enters a compressor and is compressed to a higher pressure, resulting in a higher temperature as well. The hot, compressed refrigerant vapor is now at a temperature and pressure at which it can be condensed and is routed through a condenser line to the condenser. At the condenser, the vapor is cooled by air flowing across the condenser coils and condensed into a liquid. Thus, the circulating refrigerant rejects heat from the system and the heat is carried away by the air.

The condensed and pressurized liquid refrigerant is next routed through an expansion valve where it undergoes an abrupt reduction in pressure. That pressure reduction results in flash evaporation of a part of the liquid refrigerant, lowering its temperature. The cold refrigerant is then routed through the evaporator. A fan blows the warm air, which is to be cooled, across the evaporator, causing the liquid part of the cold refrigerant mixture to evaporate as well; thus further lowering the temperature. The warm air is consequently cooled. To complete the refrigeration cycle, the refrigerant vapor is routed back into the compressor through a condensation line.

The condensation line discharges excess condensate formation. It is known that condensate formation is problematic to air conditioners and other refrigeration systems. When humid air contacts an air conditioner's cold evaporator coils, moisture from the air condenses on the coils. The condensed moisture, called "condensate," must be collected and disposed of to prevent water damage to property in the vicinity of the air conditioner.

Often, the collection of the condensate that drips off the air conditioner's evaporator coils, involves the use of a drain pan placed below the coils. The condensate collected in the drain pan is then carried through a condensation discharge line to a sewer system or an outside area. A common problem occurring with condensate drain pipes has been that biotic growth, such as algae or fungus, formed in the pipes blocks the flow of condensate. The blockage caused by this biotic growth results in condensate backing up in the drain pan and ultimately spilling over into the surrounding area. The collection of condensate encourages the growth of bacteria, algae, and other organisms that block the condensation line. Further, because the drainage system is out of sight, it may be neglected until damage occurs to the lines and components of the air conditioning unit.

It is known that a biocide is a chemical substance or microorganism which can deter, render harmless, or exert a controlling effect on any harmful organism by chemical or biological means. Biocides can be added to the condensation line to inhibit the growth of bacteria, algae, and other organisms that block the condensation line.

Even though the above cited systems and methods for dispensing a biocide into a condensation line address some of the needs of the market, a device that easily attaches to the condensation line and controllably releases the biocide through the utilization of a time release pump is still desired. Devices that dispense biocide into condensation lines and cold-lines have been used for inhibiting algae in the past, yet none with the present characteristics of the present invention. See patent numbers: U.S. Pat. No. 4,962,778; U.S. Pat. No. 5,402,813; U.S. Pat. No. 7,686,034 and U.S. 20130306163.

SUMMARY OF THE INVENTION

The present invention is directed to a time release biocide dispensing device that is efficacious for controllably dispensing a biocide into a line at predetermined concentrations and volumes over a duration. The device utilizes basic principles of pressure equilibrium and material resistance to dispense a regulated and steady flow of the biocide into the line. The device utilizes a controller, a pump, a container, a fluid tube, and a coupling member to ensure that a steady supply of biocide is dispensed into the line. The device is also configured to easily attach to the line and facilitate setting of the controller, such that minimal tools and expertise are needed for operation.

In one embodiment, a condensate fluid from a collection pan near an air conditioning unit passes through a condensation line. The biocide is stored in a container, which is configured to attach along a longitudinal axis of the condensation line. The container is oriented in relation to the condensation line so that a vacuum forms in a volume above the biocide. The vacuum inhibits the biocide from dispensing from the container into the condensation line.

A controller controllably pumps a fluid into the volume containing the vacuum. This higher pressure entering the volume disturbs the equilibrium, and thus forces the biocide out of the container and into the condensation line. Further, a resistance barrier positions at a dispensing aperture in the container. The resistance barrier also contributes to regulating the release of the biocide by restricting the biocide from flowing freely from the container. The controller works in conjunction with the resistance barrier to dispense a predetermined concentration and volume of the biocide into the condensation line.

In one aspect, a biocide dispensing device for regulating the release of a biocide into a line, the device comprises:
- a container configured to contain a biocide, the container at least partially comprising a volume having a vacuum, wherein the vacuum is at an equilibrium pressure with the biocide, the container further comprising a dispensing aperture configured to enable at least partial passage of the biocide;
- a pump configured to force a fluid into the volume, wherein the fluid at least partially disturbs the equilibrium pressure to at least partially enable the biocide to dispense through the dispensing aperture;
- a controller configured to regulate the pump; and
- a resistance barrier disposed in proximity to the dispensing aperture, the resistance barrier configured to at least partially inhibit the free flow of the biocide through the dispensing aperture.

In another aspect, the line comprises a condensation line for an air conditioning unit.

In another aspect, the container comprises a substantially cylinder shaped bottle.

In another aspect, the container comprises an upper region and a lower region.

In another aspect, the container couples to the line at a T junction.

In another aspect, the container is oriented in relation to the line such that the lower region positions above the upper region.

In another aspect, the lower region comprises the volume having the vacuum, and the upper region comprises the biocide.

In yet another aspect, the fluid flows from the pump to the volume through a fluid tube.

In yet another aspect, the fluid comprises air.

In yet another aspect, the pump comprises a micro air pump.

In yet another aspect, the controller comprises a circuitry.

In yet another aspect, the dispensing aperture couples to the T junction through a molded cap.

In yet another aspect, the molded cap comprises a threaded inner surface configured to rotatably attach to a 0.5" male threaded PVC pipe at the T junction.

In yet another aspect, the circuitry comprises a timer, a switch, and at least one light emitting diode.

In yet another aspect, the resistance barrier comprises a sponge.

One objective of the present invention is to provide a biocide delivery system for air conditioning condensation lines that allows the steady release of a biocide over a duration.

Another objective is to help prevent mold and sludge build up in the condensation line.

Another objective is to provide a biocide dispensing device that easily attaches to a T junction along the condensation line.

Another objective is to combine the effects of pressure equilibrium in a container of biocide, and a sponge's capacity to restrict flow of a fluid to regulate the dispensing of the biocide.

Figure 2:
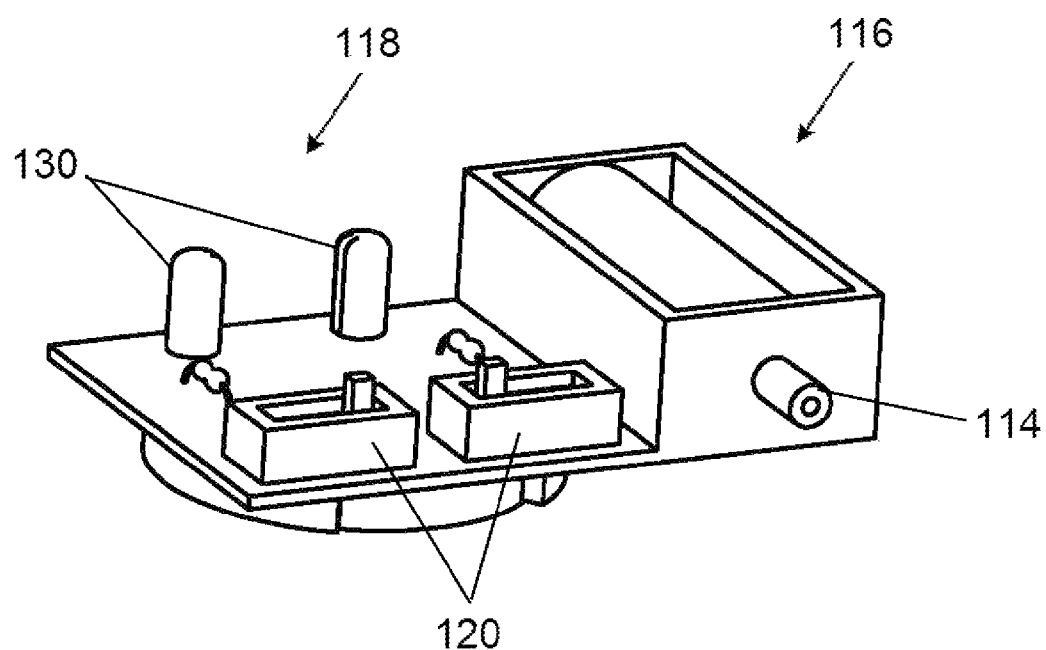
Figure 3:
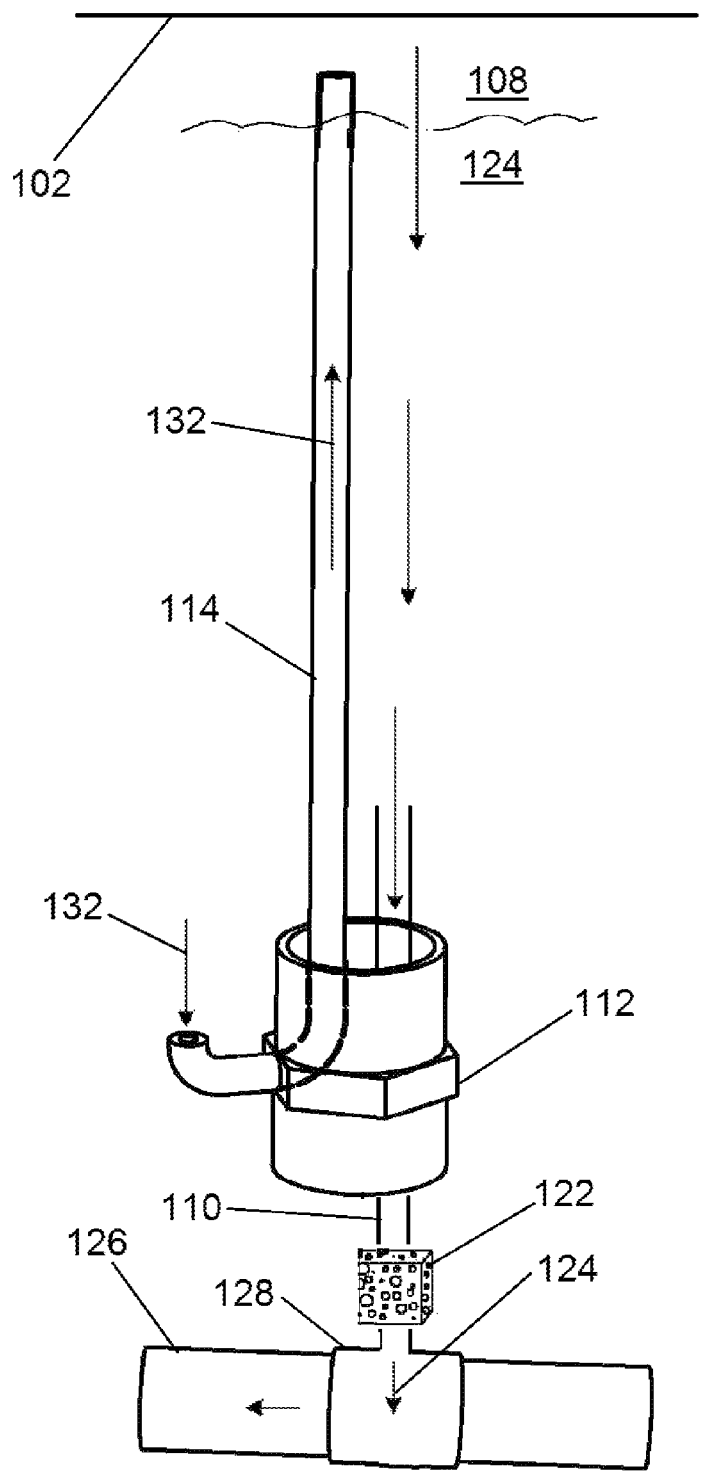

Yet another objective is to provide a biocide dispenser that enables a user to determine the concentration and volume of biocide released into a condensation line.

Yet another objective is to provide a biocide dispensing device that is inexpensive to manufacture and maintain.

These and other advantages of the invention will be further understood and appreciated by those skilled in the art by reference to the following written specification, claims and appended drawings.

BRIEF DESCRIPTION OF THE DRAWINGS

The invention will now be described, by way of example, with reference to the accompanying drawings, in which:

FIG. 1 illustrates a sectioned view of a biocide dispensing device, where an exemplary fluid tube carries a fluid into a volume having a vacuum and an exemplary resistance member partially inhibits the free flow of the biocide into an exemplary line, in accordance with an embodiment of the present invention;

FIG. 2 illustrates a detailed perspective view of an exemplary controller operatively attached to an exemplary pump, in accordance with an embodiment of the present invention; and FIG. 3 illustrates a sectioned perspective view of an exemplary fluid passing through a fluid tube and creating sufficient pressure in a volume of the container to dispense a biocide through a dispensing aperture, in accordance with an embodiment of the present invention.

Like reference numerals refer to like parts throughout the various views of the drawings.

DETAILED DESCRIPTION OF THE INVENTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper," "lower," "left," "rear," "right," "front," "vertical," "horizontal," and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

At the outset, it should be clearly understood that like reference numerals are intended to identify the same structural elements, portions, or surfaces consistently throughout the several drawing figures, as may be further described or explained by the entire written specification of which this detailed description is an integral part. The drawings are intended to be read together with the specification and are to be construed as a portion of the entire "written description" of this invention as required by 35 U.S.C. §112.

In one embodiment of the present invention presented in FIGS. 1-3, a time release biocide dispensing device 100 for controllably dispensing a biocide 124 into a line 126 at predetermined concentrations and volumes over a predetermined duration. In this manner, a steady, controllable stream of biocide 124 can enter a line 126 to help prevent biological and sludge buildup in the line 126. The device 100 easily attaches to the line 126, such that minimal tools and expertise are needed to attach the device 100 to the line 126.

In some embodiments, the line 126 may include, without limitation, a condensation line for an air conditioning unit, a cold-line, a refrigerant line, a drain pipe, a waste gulley, a hose line 126, and different components of an HVAC system. The biocide 124 is effective in destroying the bacteria and organic buildup in the line 126 without damaging the interior lining of the line 126 itself. In one embodiment, the biocide 124 may be present in the form of a liquid. However, in other embodiments a solid tablet of biocide 124 may be dissolved and stored within the device 100 prior to dispensing into the line 126. The biocide 124 may include, without limitation, a natural biocide, a synthetic biocide, white vinegar, bleach, and a chemical substance or microorganism which can deter, render harmless, or exert a controlling effect on any harmful organism by chemical or biological means.

As referenced in FIG. 1, the device 100 attaches to a T junction 128 in the line 126. A molded cap 112 can form a coupling mechanism to fasten the device 100 to the T junction 128. However, in other embodiments, the device 100 may position at a distance from the line 126, such as at an air conditioning unit. A biocide tube may then carry the dispensed biocide 124 to a desired location along the line 126. The device 100 utilizes basic principles of pressure equilibrium and material resistance to dispense a regulated and steady flow of the biocide 124 into the line 126.

In some embodiments, the device 100 may include a controller 118, a pump 116, a container 102, a fluid tube 114, and a coupling molded cap 112 to operate; thereby ensuring a steady supply of biocide 124 is dispensed into the line 126. The device comprises a container 102 configured to at least partially contain a biocide 124. In one embodiment, the container 102 comprises a substantially cylinder shaped bottle. However, in other embodiments, any housing that is sized and dimensioned to contain the biocide 124 and position proximally to the line 126 may be used. The container 102 couples to the line 126 at a T junction 128 along a longitudinal axis of the line 126.

The container 102 comprises an upper region 106 and a lower region 104. The container 102 is oriented in relation to the line 126 such that the lower region 104 positions above the upper region 106. Those skilled in the art will recognize that filling the container 102 partially with a liquid and then reorienting the container 102 over itself creates a vacuum in the empty region of the container 102. The container 102 at least partially comprises a volume 108 having a vacuum, wherein the vacuum is at an equilibrium pressure with the biocide 124. In one embodiment, the lower region 104 comprises the volume 108 having the vacuum, and the upper region 106 comprises the biocide 124.

The container 102 further comprises a dispensing aperture 110 that aligns adjacently to the T junction 128 on the line 126 to enable at least partial passage of the biocide 124 into the line 126. In one embodiment, the dispensing aperture 110 couples to the T junction 128 through a molded cap 112. In another embodiment, the molded cap 112 comprises a threaded inner surface configured to rotatably mate with a 0.5" male threaded PVC pipe at the T junction 128. However, in other embodiments, the molded cap 112 may frictionally snap, magnetically attach, and be fastened by screws to the T junction 128.

Turning now to FIG. 2, the device 100 comprises a pump 116 configured to force a fluid 132 into the empty volume 108 within the container 102. The fluid 132 flows from the pump 116 to the volume 108 through a fluid tube 114. The fluid tube 114 is sufficiently flexible to follow a circuitous route from the pump 116 to the container 102 while still maintaining a pressure. The pressure from the fluid 132 disturbs the pressure equilibrium between the volume 108 and the biocide 124, and thus forces the biocide 124 to dispense through the lower region 104 of the container 102. The pump 116 may include a micro air pump 116. However, any pump 116 having sufficient capacity to generate and force the fluid 132 into the fluid tube 114 to the container 102 may be used. The fluid 132 may include air generated by the pump 116 to at least partially disturb the equilibrium pressure. Once the equilibrium is disturbed the biocide 124 dispenses through the dispensing aperture 110.

As referenced in FIG. 3, a controller 118 controllably regulates the pump 116, which generates and forces a fluid 132 into the volume 108 of the container 102. This higher pressure entering the volume 108 disturbs the equilibrium, and thus forces the biocide 124 out of the container 102 and into the line 126. The controller 118 comprises a circuitry configured to regulate the pump 116. In one embodiment, the circuitry comprises a timer (not shown), at least one switch 120, and at least one light emitting diode 130. The circuitry is configured to regulate the duration that the pump 116 operates with the timer. In one embodiment, the circuit may include a 5 5 5 integrated circuit having a timer. However in other embodiments, the timer is integrated into the at least one switch 120. In any case, the duration that the pump 116 operates may be controlled.

In one alternative embodiment, a pin valve (not shown), rather than the pump 116 is used to disturb the equilibrium between the volume 108 and the biocide 124 in the container 102. In this configuration, the controller 118 regulates the pin valve, which is located at the lower region 104 of the container 102. The pin valve opens to enable passage of the fluid 132 from the fluid tube 114 to pass into the volume 108. The pin valve can also close to restrict passage of the fluid 132 into the container 102. Nonetheless, the basic premise of disturbing the equilibrium between the vacuum and the biocide 124 to dispense the biocide 124 into the line 126 remains the same for either the pin valve or the pump 116.

FIG. 3 further illustrates a resistance barrier 122 disposed in proximity to the dispensing aperture 110. The resistance barrier 122 is configured to at least partially inhibit the free flow of the biocide 124 through the dispensing aperture 110. The resistance barrier 122 may include, without limitation, a sponge, a filter, a valve, and an object having a capacity to absorb and release a liquid. Those skilled in the art will recognize that a sponge's capacity to restrict flow of a fluid 132 can be effective in regulating the dispensing of the biocide 124. The resistance barrier 122 works in conjunction 128 with the controller 118 to dispense a predetermined concentration and volume of the biocide 124 into the condensation line 126. Thus, the device 100 relies on two bottle neck effects to regulate the dispensing of the biocide 124: the pump 116 forces fluid 132 into the container 102 for a duration, and the resistance barrier 122 regulates the final dispensing of biocide 124 into the line 126. This double regulation creates a more precise, cost effective dispensing solution for the biocide 124.

In one example, without limitation, a condensate fluid from a collection pan near an air conditioning unit passes through a condensation line. The biocide 124 is stored in a container 102, which is configured to attach along a longitudinal axis of the condensation line 126. The container 102 is oriented in relation to the condensation line 126 so that a vacuum forms in a volume 108 above the biocide 124. The vacuum inhibits the biocide 124 from dispensing from the container 102 into the condensation line 126. As the pump 116 forces air into the vacuum in the volume 108, the biocide drips through the dispensing aperture 110 and a sponge, into the condensation line. The amount of biocide 124 dripping into the condensation line is controlled by the timer in the controller 118.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalence.

What we claim is:

1. A biocide dispensing device for regulating the release of a biocide into a line, the device comprises:
- a container configured to at least partially contain a biocide, the container at least partially comprising a volume having a vacuum, wherein the vacuum is at an equilibrium pressure with the biocide, the container further comprising a dispensing aperture configured to enable at least partial passage of the biocide, the container further comprising an upper region and a lower region, the lower region comprising the volume having the vacuum, and the upper region comprising the biocide, the container oriented in relation to the line such that the lower region positions above the upper region;
- a pump configured to force a fluid into the volume, wherein the fluid at least partially disturbs the equilibrium pressure to at least partially enable the biocide to dispense through the dispensing aperture;
- a fluid tube, the fluid tube configured to convey the fluid from the pump to the volume;
- a controller configured to regulate the pump; and
- a resistance barrier disposed in proximity to the dispensing aperture, the resistance barrier configured to at least partially inhibit the free flow of the biocide through the dispensing aperture.

2. The device of claim 1, wherein the line comprises a condensation line for an air conditioning unit.

3. The device of claim 2, wherein the container comprises a substantially cylinder shaped bottle.

4. The device of claim 3, wherein the container couples to the line at a T junction.

5. The device of claim 4, wherein the dispensing aperture couples to the T junction through a molded cap.

6. The device of claim 5, wherein the molded cap comprises a threaded inner surface configured to rotatably attach to a 0.5" male threaded PVC pipe at the T junction.

7. The device of claim 1, wherein the fluid comprises air.

8. The device of claim 1, wherein the pump comprises a micro air pump.

9. The device of claim 1, wherein the controller comprises a circuitry, the circuitry comprising a timer, at least one switch, and at least one light emitting diode.

10. The device of claim 1, wherein the resistance barrier comprises a sponge.

11. A biocide dispensing device for regulating the release of a biocide into a line, the device comprises:
- a container configured to at least partially contain a biocide, the container at least partially comprising a volume having a vacuum, wherein the vacuum is at an equilibrium pressure with the biocide, the container further comprising a dispensing aperture configured to enable at least partial passage of the biocide, the container further comprising an upper region and a lower region, the lower region comprising the volume having the vacuum, and the upper region comprising the biocide, the container oriented in relation to the line such that the lower region positions above the upper region;
- a valve disposed to attach to the container, the valve configured to enables passage of a fluid into the volume, wherein the fluid at least partially disturbs the equilibrium pressure to at least partially enable the biocide to dispense through the dispensing aperture;
- a controller configured to regulate the valve; and
- a resistance barrier disposed in proximity to the dispensing aperture, the resistance barrier configured to at least partially inhibit the free flow of the biocide through the dispensing aperture.

12. The device of claim 11, wherein the line comprises a condensation line for an air conditioning unit.

13. The device of claim 12, wherein the controller comprises a circuitry, the circuitry comprising a timer, a switch, and at least one light emitting diode.

14. The device of claim 13, wherein the container comprises an upper region and a lower region, the container oriented in relation to the line such that the lower region positions above the upper region.

15. The device of claim 14, wherein the lower region comprises the volume having the vacuum, and the upper region comprises the biocide.

16. The device of claim 15, wherein the valve is disposed to attach to the lower region.

17. The device of claim 16, wherein the valve comprises a pin valve.

18. A biocide dispensing device for regulating the release of a biocide into a line, the device comprises:
- a container configured to at least partially contain a biocide, the container at least partially comprising a volume having a vacuum, wherein the vacuum is at an equilibrium pressure with the biocide, the container further comprising a dispensing aperture configured to enable at least partial passage of the biocide, the container further comprising an upper region and a lower region, the lower region comprising the volume having the vacuum, and the upper region comprising the biocide, the container oriented in relation to the line such that the lower region positions above the upper region;
- a pump configured to force a fluid into the volume, wherein the fluid at least partially disturbs the equilibrium pressure to at least partially enable the biocide to dispense through the dispensing aperture;
- a fluid tube, the fluid tube configured to convey the fluid from the pump to the volume;
- a controller configured to regulate the pump;
- a sponge disposed in proximity to the dispensing aperture, the sponge configured to at least partially inhibit the free flow of the biocide through the dispensing aperture; and
- a circuitry, the circuitry comprising a timer, the timer configured to regulate the duration that the pump operates.

19. The device of claim 18, wherein the circuitry further includes a switch and at least one light emitting diode.

20. The device of claim 19, wherein the pump comprises a micro air pump.

* * * * *